US012806626B2

(12) United States Patent
Wolf et al.

(10) Patent No.: US 12,806,626 B2
(45) Date of Patent: *Nov. 24, 2026

(54) ANTIMICROBIAL LED DISPOSER SYSTEM AND METHOD

(71) Applicant: INSINKERATOR LLC, Benton Harbor, MI (US)

(72) Inventors: Eric Wolf, Waterford, WI (US); Cori Winslow, Rensselaer, NY (US); Jonas Ciemny, Colonie, NY (US); Charles A. Farago, Kenosha, WI (US)

(73) Assignee: INSINKERATOR LLC, Benton Harbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 19/450,271

(22) Filed: Jan. 15, 2026

(65) Prior Publication Data

US 2026/0137825 A1 May 21, 2026

Related U.S. Application Data

(63) Continuation of application No. 18/743,992, filed on Jun. 14, 2024.

(60) Provisional application No. 63/612,649, filed on Dec. 20, 2023, provisional application No. 63/521,165, filed on Jun. 15, 2023.

(51) Int. Cl.

| | |
|---|---|
| ***B02C 19/18*** | (2006.01) |
| ***A61L 2/084*** | (2026.01) |
| ***A61L 2/26*** | (2006.01) |
| ***B02C 18/12*** | (2006.01) |

(52) U.S. Cl.

CPC .............. *B02C 19/18* (2013.01); *A61L 2/084* (2013.01); *A61L 2/26* (2013.01); *B02C 18/12* (2013.01); *A61L 2202/11* (2013.01)

(58) Field of Classification Search

CPC ......... A61L 2/26; A61L 2/084; A61L 2202/11

See application file for complete search history.

(56) References Cited

U.S. PATENT DOCUMENTS 2,946,522 A 7/1960 Green
4,955,657 A 9/1990 Ward
(Continued)

FOREIGN PATENT DOCUMENTS

CN 103104011 A 5/2013
CN 204983109 U 1/2016
(Continued)

OTHER PUBLICATIONS

Sep. 4, 2024 International Search Report and Written Opinion from the International Searching Authority for International Application No. PCT/US2024/034111 (13 pages).

*Primary Examiner* — Christine J Skubinna
(74) *Attorney, Agent, or Firm* — Brooks Kushman, P.C.

(57) ABSTRACT

Disposer systems having antimicrobial lighting, lens assemblies for use in disposer systems, and methods of installing antimicrobial lighting into disposer systems are provided. The lens assemblies include a lens that forms an inner wall of the lens assembly and faces into an interior area of the disposer system, at least one LED board including at least one LED that emits violet light. Lens assemblies may be secured to at least one of a waste disposer, a sink flange or a mounting gasket of the waste disposer system.

15 Claims, 15 Drawing Sheets

(56) References Cited

U.S. PATENT DOCUMENTS

| | | | | |
|---|---|---|---|---|
| 5,662,404 | A | 9/1997 | Susat | |
| 6,502,976 | B1 | 1/2003 | Bernhard | |
| 7,604,190 | B2 | 10/2009 | Pai | |
| 7,735,763 | B2 | 6/2010 | Bell et al. | |
| 7,900,288 | B2 | 3/2011 | Fima | |
| 11,306,467 | B2 | 4/2022 | Paweleck et al. | |
| 11,369,704 | B2 | 6/2022 | Winslow et al. | |
| 2004/0256506 | A1 | 12/2004 | Berger | |
| 2011/0272506 | A1 | 11/2011 | Boland et al. | |
| 2013/0327860 | A1 | 12/2013 | Harooni | |
| 2015/0202633 | A1 | 7/2015 | Perkins | |
| 2015/0369471 | A1 | 12/2015 | Williams | |
| 2019/0106869 | A1 | 4/2019 | Radl et al. | |
| 2020/0206373 | A1 | 7/2020 | Winslow et al. | |
| 2021/0085810 | A1 | 3/2021 | Barron et al. | |
| 2021/0198879 | A1 | 7/2021 | Munn | |
| 2021/0353813 | A1* | 11/2021 | Wald | A61L 9/22 |
| 2022/0274119 | A1* | 9/2022 | Sandoval | E03C 1/2665 |

FOREIGN PATENT DOCUMENTS

| | | | | |
|---|---|---|---|---|
| CN | 106925410 | B | 7/2019 | |
| CN | 218814130 | U | 4/2023 | |
| EP | 2207622 | B1 | 9/2015 | |
| JP | 5945135 | B2 | 7/2016 | |
| KR | 1020170001854 | A | 1/2017 | |
| KR | 102275831 | B1 * | 7/2021 | F21V 33/00 |
| KR | 102443576 | B1 | 9/2022 | |
| KR | 1020220165021 | A | 12/2022 | |

* cited by examiner

ANTIMICROBIAL LED DISPOSER SYSTEM AND METHOD

CROSS-REFERENCE TO RELATED APPLICATIONS

This application is a continuation of U.S. application Ser. No. 18/743,992 filed Jun. 14, 2024, which claims priority to U.S. Provisional Application Ser. No. 63/521165, entitled "Antimicrobial LED Sink Flange Apparatus and Method", filed on Jun. 15, 2023, and U.S. Provisional Application Ser. No. 63/612649, entitled "Antimicrobial LED Sink Flange Apparatus and Method", filed on Dec. 20, 2023, the disclosures of which are hereby incorporated by reference in their entirety.

FIELD OF INVENTION

The present technology relates to components of sinks and food waste disposers that are installed under sinks, and more particularly to components of sinks and food waste disposers that include anti-microbial LED (Light Emitting Diode) lighting.

BACKGROUND

Food waste disposers are used to comminute food scraps into particles small enough to pass through household drain plumbing. Referring to FIG. 1 (Prior Art), a conventional food waste disposer 10 is often mounted to a sink, such as a kitchen sink (126 in FIG. 2), and includes a food conveying section 12, a motor section 14, and a grinding section 16 disposed between the food conveying section 12 and the motor section 14. The food conveying section 12 includes a housing 18 that forms an inlet for receiving food waste and water. The food conveying section 12 conveys the food waste to the grinding section 16, and the motor section 14 includes a motor imparting rotational movement to a motor shaft to operate the grinding section.

Referring to FIGS. 1 and 2, food waste disposers such as the food waste disposer 10 are generally installed to a sink 126 in a two-step procedure using a mounting assembly 100, an example of which is shown in FIG. 1 (Prior Art) in an exploded manner relative to the food waste disposer 10. First, a sink flange assembly 102, which includes a sink (or strainer) flange 104, a sink gasket 106, a back-up flange 108, an upper mounting flange 110, bolts 112, and a retaining ring 114 are installed or mounted in relation to the sink 202. Second, a disposer assembly 30 including the food waste disposer 10 and also including a mounting (or sealing) gasket 116 and a lower mounting flange 118 are attached to the sink flange assembly 102. The combination of the disposer assembly 30 and the mounting assembly 100 can be considered to constitute an overall food waste disposer assembly 124.

More particularly with respect to the attachment of the disposer assembly 30 to the sink flange assembly 102, it should be understood that the lower mounting flange 118 is placed around the housing 18 that forms the inlet of the food conveying section 12. The mounting gasket 116 is then placed around that inlet as well, above the lower mounting flange 118, in a manner tending to secure the mounting gasket 116 to the inlet, by virtue of a lip at the inlet of the housing 18. Attachment of the disposer assembly 30 including the food waste disposer 10 to the sink flange assembly 102 and thereby to the sink is then particularly achieved by engaging mounting tabs 120 of the lower mounting flange 118 with ramps (or inclined mounting fasteners or edges or ridges) 122 of the upper mounting flange 110 and then rotating the lower mounting flange 118 relative to the upper mounting flange 110 until secure. When the lower mounting flange 118 and upper mounting flange 110 are secured together, the mounting gasket 116 is compressed therebetween.

Referring to FIG. 2, the food waste disposer assembly 124 is shown installed or mounted in relation to a sink 126. Although FIG. 2 shows a side elevation view of the food waste disposer assembly 124, FIG. 2 provides a cutaway cross-sectional view of the sink 126, so as to better illustrate how the food waste disposer assembly 124 is installed relative to the sink 126. The food waste disposer assembly 124 particularly includes the disposer assembly 30 that includes the food waste disposer 10 and the mounting assembly (or sink flange assembly) 100 that allows for the disposer assembly 124 to be attached to the sink 126.

SUMMARY

Disposer systems having lens assemblies that provide antimicrobial lighting, lens assemblies providing antimicrobial lighting, and methods of installing antimicrobial lighting into disposer systems and components of disposers are disclosed herein.

In one aspect, a waste disposer system having antimicrobial lighting is provided, the waste disposer system comprising: a waste disposer; a mounting assembly configured to mount the waste disposer to a sink, the mounting assembly comprising a sink flange assembly and a mounting gasket that connects the sink flange assembly to the waste disposer; and a lens assembly secured to at least one of the waste disposer, the sink flange or the mounting gasket, the lens assembly including at least one lens that forms an inner wall of the lens assembly and faces into an interior area of the waste disposer system, and at least one LED board including at least one light emitting diode that emits violet light.

In another aspect, a lens assembly for use in a waste disposer system is provided, the lens assembly comprising: at least one lens that forms an inner wall of the lens assembly and is configured to face into an interior area of the waste disposer system; and at least one LED board including at least one light emitting diode that emits violet light.

In a third aspect, a method of installing antimicrobial lighting in a waste disposer system that includes a waste disposer and a mounting assembly configured to mount the waste disposer to a sink is provided. The mounting assembly comprises a sink flange assembly and a mounting gasket that connects the sink flange assembly to the waste disposer. The method comprises: providing a lens assembly, wherein the lens assembly includes a lens that forms an inner wall of the lens assembly and faces into the interior area, and at least one LED board including at least one LED that emit violet light; and securing the lens assembly to at least one of the waste disposer, the sink flange or the mounting gasket.

BRIEF DESCRIPTION OF THE DRAWINGS

Specific examples have been chosen for purposes of illustration and description, and are shown in the accompanying drawings, forming a part of the specification.

Figure 1:
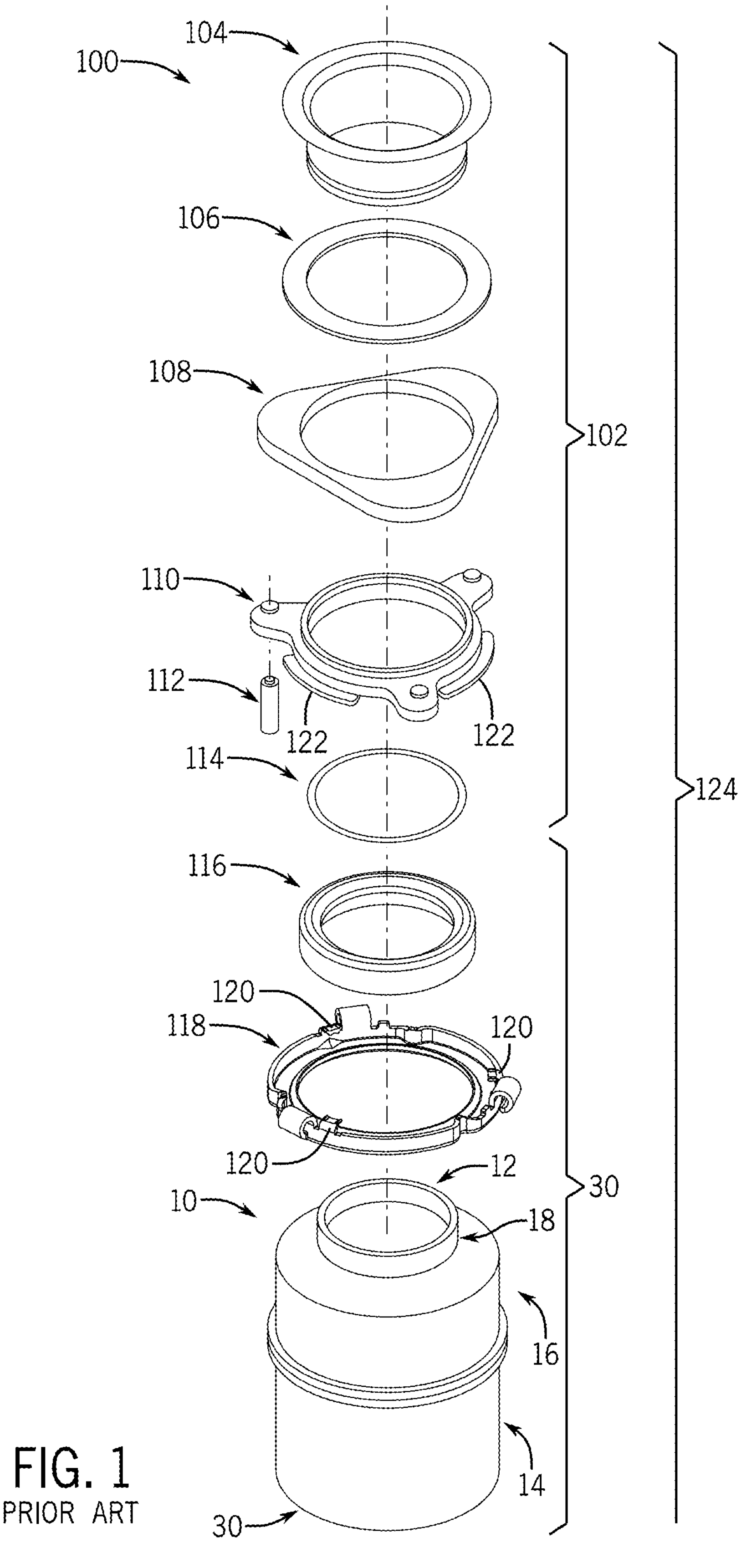
FIG. 1 PRIOR ART
FIG. 1 is an exploded view of a Prior Art food waste disposer assembly including both a mounting assembly and a disposer assembly including a food waste disposer, as can be installed in relation to another structure such as a sink.
Figure 2:
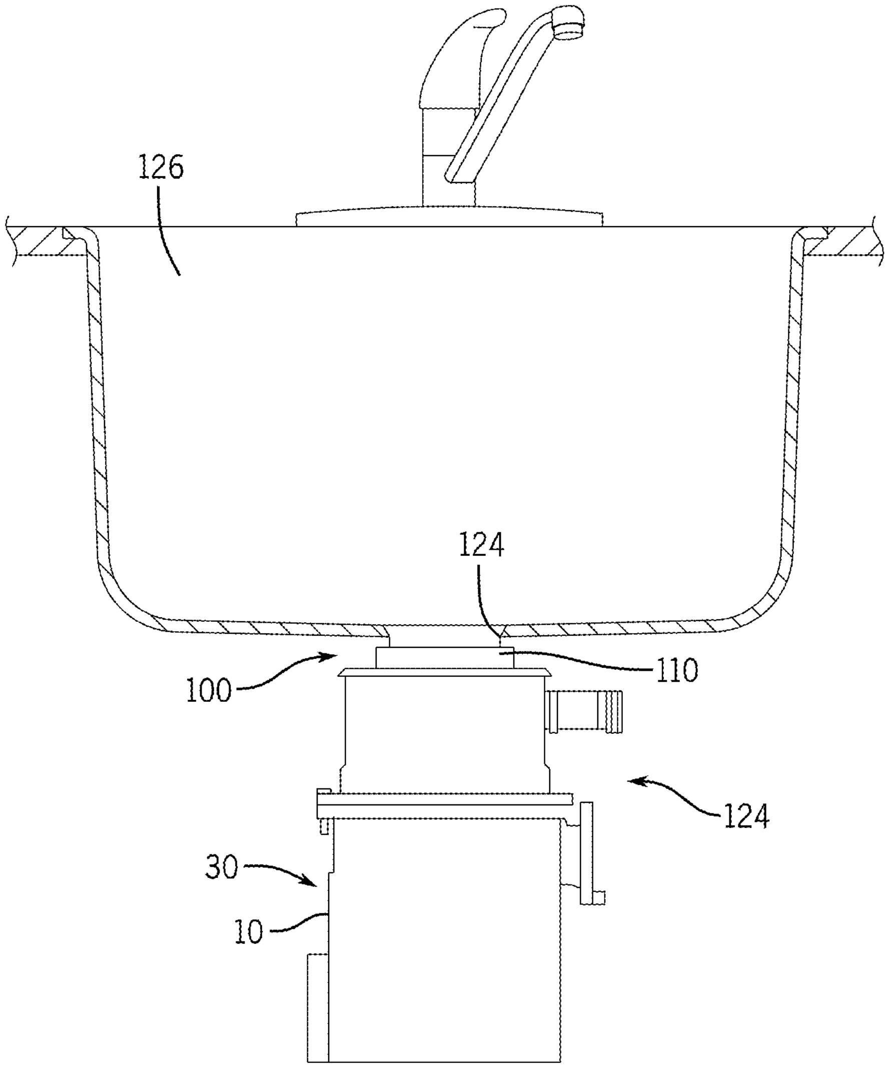
FIG. 2 PRIOR ART
FIG. 2 is a partly cross-sectional, partly front elevation view of the food waste disposer assembly of FIG. 1 mounted in relation to a sink

While various embodiments discussed herein are amenable to modifications and alternative forms, aspects thereof have been shown by way of example in the drawings and are described in detail herein. It should be understood, however, that the disclosure is not limited to the particular embodiments described, and instead is meant to include all modifications, equivalents, and alternatives falling within the scope of the disclosure. In addition, the terms "example" and "embodiment" as used throughout this application is only by way of illustration, and not limitation. The term "about" as used herein means the stated value or measurement plus or minus a 10% margin of error. The term "configured to" as used herein with respect to a component being "configured to" have certain structural characteristics in specified circumstances or to perform a function means that the component is structurally formed such that the component meets the structural characteristics in the specified circumstances or performs the function without further modification. The Figures are not necessarily drawn to scale. The use of the same reference symbols in different drawings indicates similar or identical items unless otherwise noted.

DETAILED DESCRIPTION

Waste disposer systems that provide antimicrobial light, lens assembles that provide antimicrobial light for use in waste disposer systems, and methods of installing antimicrobial lighting in waste disposer systems are provided.

Generally, waste disposer systems of the present technology include a waste disposer, a mounting assembly configured to mount the waste disposer to a sink, and a lens assembly. The mounting assembly includes a sink flange assembly and a mounting gasket that connects, either directly or indirectly, the sink flange assembly to the waste disposer.

Lens assemblies of the present technology include at least one lens and at least one light emitting diode (LED) that emits antimicrobial light, such as violet light. In some examples, a lens assembly of the present technology may include a lens that forms an inner wall of the lens assembly and is configured to face into an interior area of the waste disposer system, and at least one LED board that includes the at least one LED that emits antimicrobial light. The lens assembly may be secured to at least one of the waste disposer, the sink flange or the mounting gasket.

Figure 12:
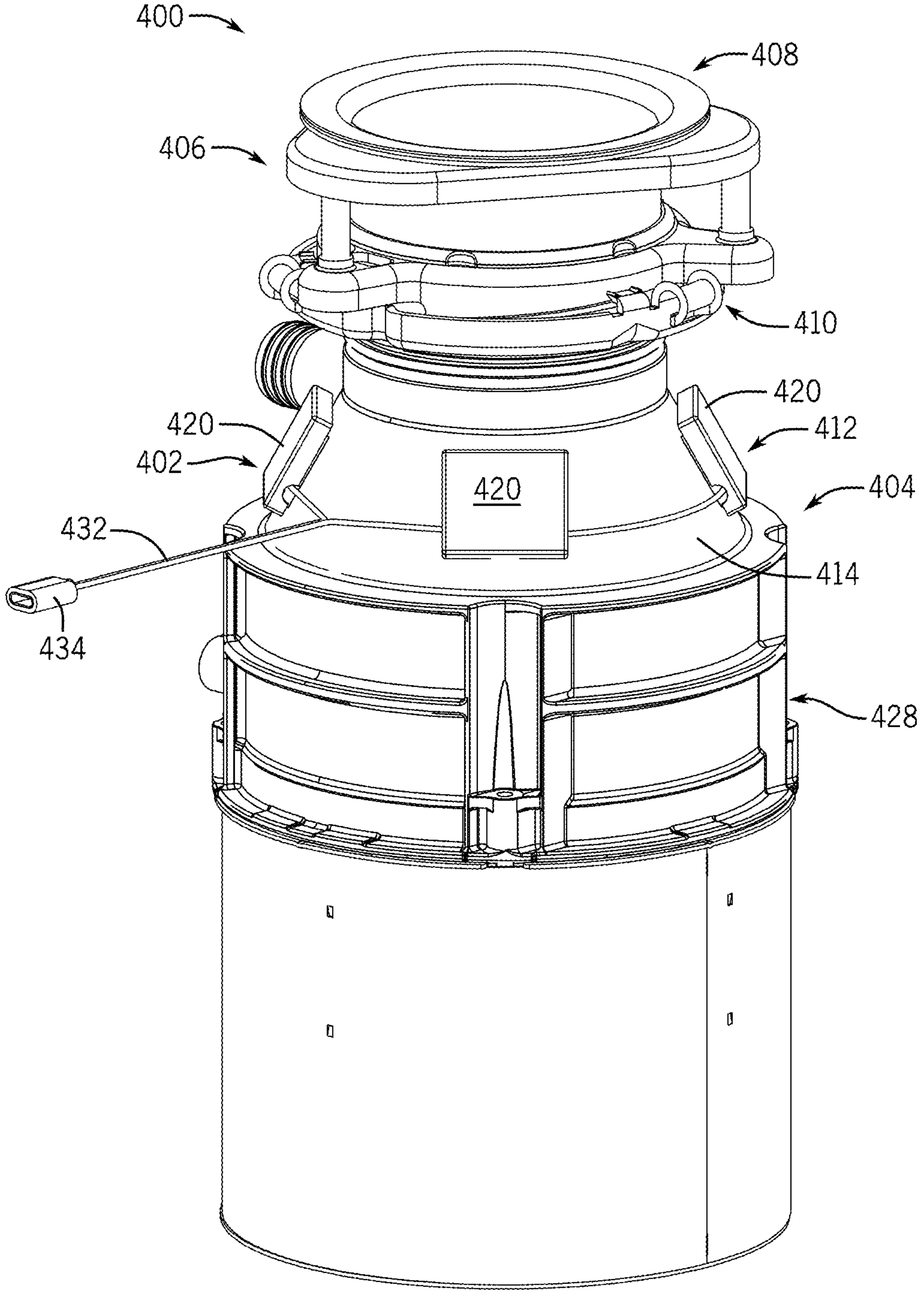
FIG. 12 illustrates a side view of as second example of a lens assembly of the present technology installed in a waste disposer system of the present technology.
Figure 13:
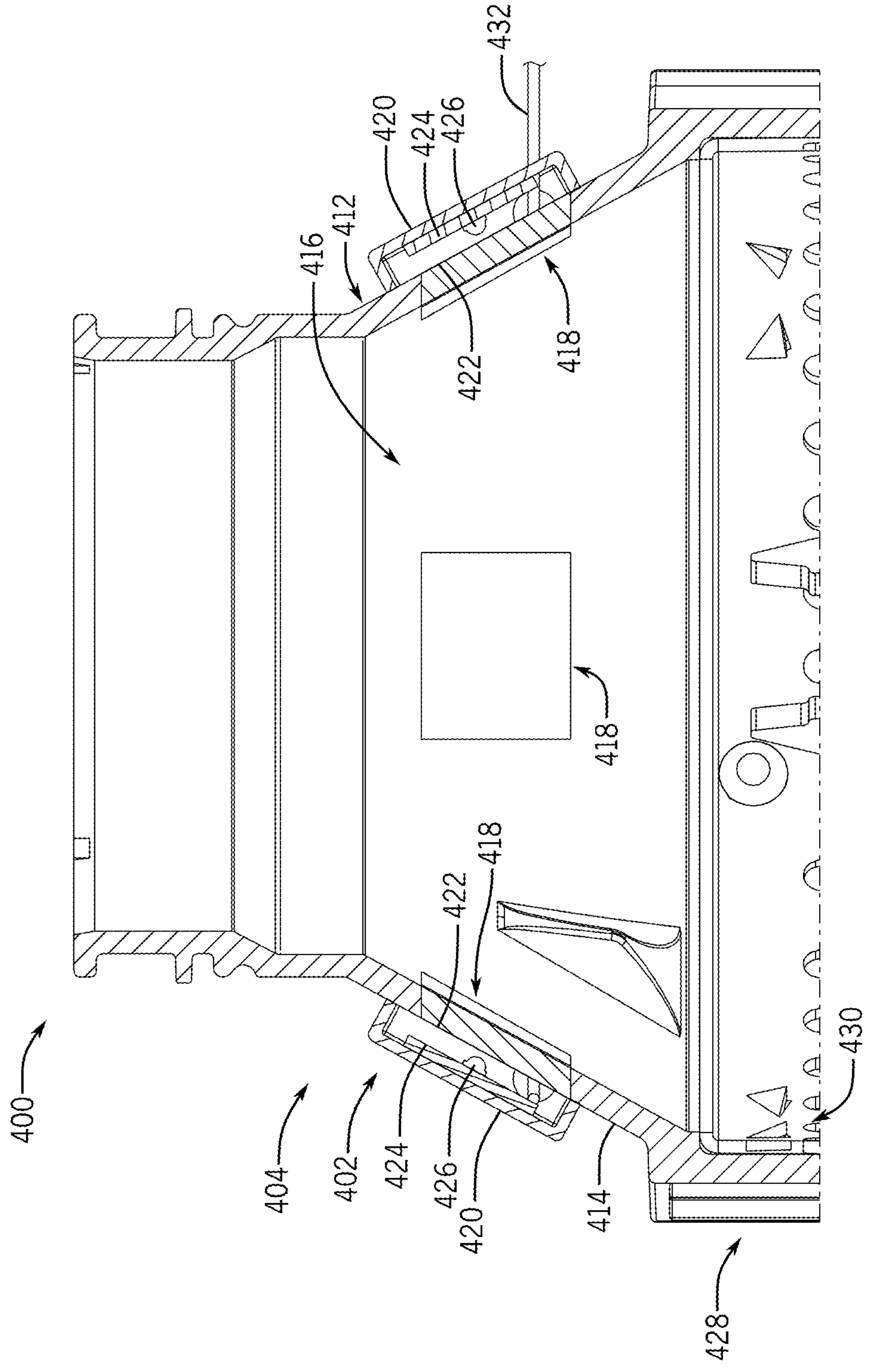
FIG. 13 illustrates a partial cross-sectional view of the lens assembly of FIG. 12.
Figure 14:
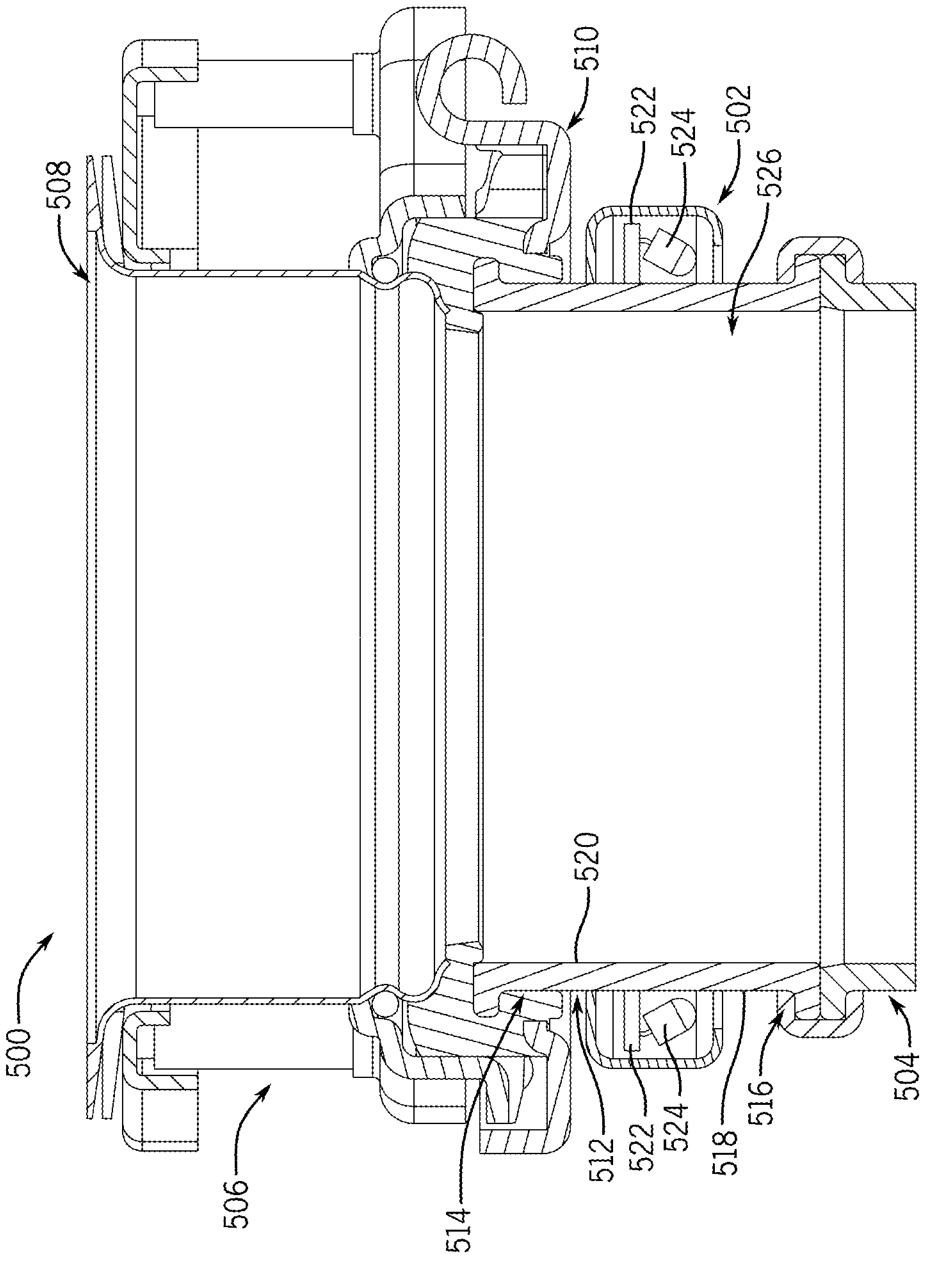
FIG. 14 illustrates a partial cross-sectional view of a third example of a lens assembly of the present technology installed in a waste disposer system of the present technology.

FIGS. 1-14 illustrate various examples of waste disposer systems and lens assemblies of the present technology. FIGS. 1-11 illustrate an example in which a lens assembly of the present technology is included in a sink flange assembly. FIGS. 12-13 illustrate an example in which a lens assembly of the present technology is installed on a portion of a waste disposer, specifically an upper portion. FIG. 14 illustrates an example in which a lens assembly of the present technology is provided in an extension tube that is configured to be installed between a mounting gasket and a waste disposer in a waste disposer system.

The terms antimicrobial light and antimicrobial lighting as used herein includes any light that tends to kill or slow the spread of microorganisms. Antimicrobial light includes violet light, such as light having a wavelength in the range from about 380 nanometers (nm) to about 750 nm, such as from about 380 nanometers (nm) to about 420 nm. Unlike ultraviolet light, violet light does not tend to cause damage to human eyes and skin. Yet, violet light has been found to reduce or prevent the growth of and may kill bacteria, fungi, yeast, mold, and mildew, particularly when used for continuous periods of time. Additional information regarding antimicrobial violet light can be found in U.S. Pat. No. 11,878,084 (U.S. patent application Ser. No. 16/577,766), entitled "Disinfecting Light Emitting Subcomponent", the contents of which are incorporated herein by reference in their entirety.

Referring to FIGS. 3-11, in some examples of the present technology, lens assemblies for use in waste disposer systems are included in a sink flange assembly.

Figure 3:
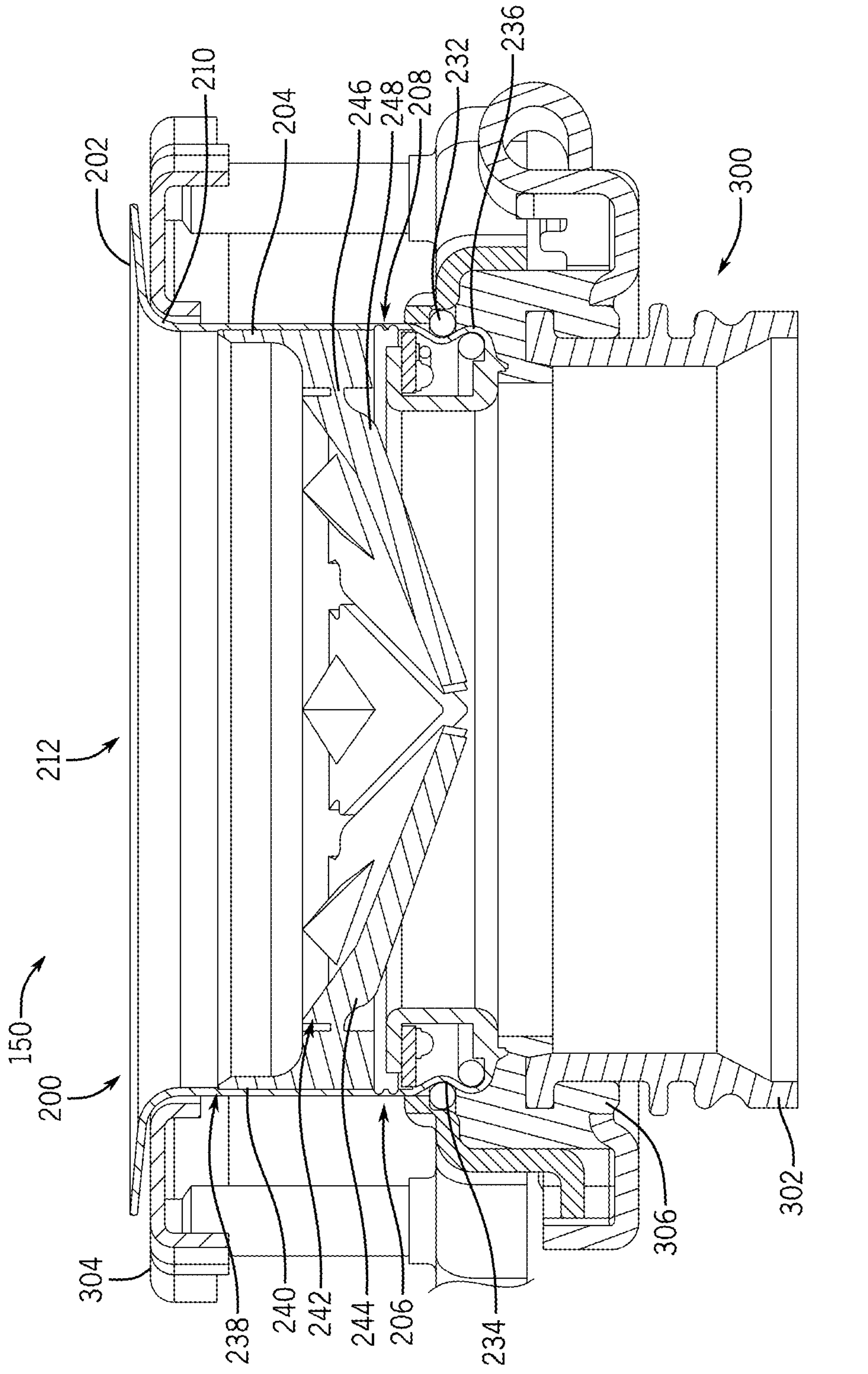
FIG. 3 illustrates a first example of a lens assembly of the present technology installed in a waste disposer system of the present technology, where the lens assembly is installed in a sink flange.

FIG. 3 illustrates a waste disposer system 150 that includes a sink flange assembly 200 and a waste disposer assembly 300. The waste disposer assembly 300 includes disposer 302, and a mounting assembly 304 that includes a mounting (or sealing) gasket 306. The sink flange assembly 200 includes a lens assembly 206 of the present technology.

Sink flange assemblies of the present technology generally include an upper portion including an annular ring that encircles the edge of the drain, and a sidewall that extends through the drain of the sink. The sidewall has a lower portion that includes a lens assembly configured to provide antimicrobial light. In various embodiments, sink flanges of the present technology may be installed in sinks with or without a disposer, such as a food waste disposer.

As shown in FIGS. 3, 4, 5, and 7 the sink flange assembly 200 includes annular ring 202 that is configured to encircle the circular edge of the sink drain when the sink flange assembly 200 is installed in a sink. The sink flange assembly also includes a sidewall 204 that is configured to be inserted and extend through the drain of the sink when the sink flange assembly 200 is installed in a sink. As used herein, the term "configured to" means that the component is structurally and functionally designed and formed to do whatever the component is said to be configured to do. The sidewall 204 may be connected to and extend downwardly from the annular ring 202. The annular ring 202 and the sidewall may be perpendicular, or substantially perpendicular, to each other. The sidewall 204 may be cylindrical, or generally cylindrical, having a circular cross-section. The sidewall 204 is connected to the annular ring 202 at a top edge 210 of the sidewall, which is opposite a lower portion 208 of the sidewall. The sidewall 204 forms an interior area 212, through which water and waste can exit the sink.

The sink flange assembly 200 further includes a lens assembly 206. The lower portion 208 of the sidewall may include the lens assembly 206. The lens assembly may be attached to, and secured within, the lower portion 208 of the sidewall 204.

Examples of the lens assembly 206 are best shown in FIGS. 6 through 9. The lens assembly 206 may include a lens 214, which is configured to allow light, at least in the violet range, to shine through the lens. The lens 214 may be made of any suitable material, such as plastic, and may be clear, substantially, clear, or translucent. The lens 214 forms an inner wall 260 of the lens assembly 206, facing into the interior area 212 of the sink flange assembly 200.

Figure 6:
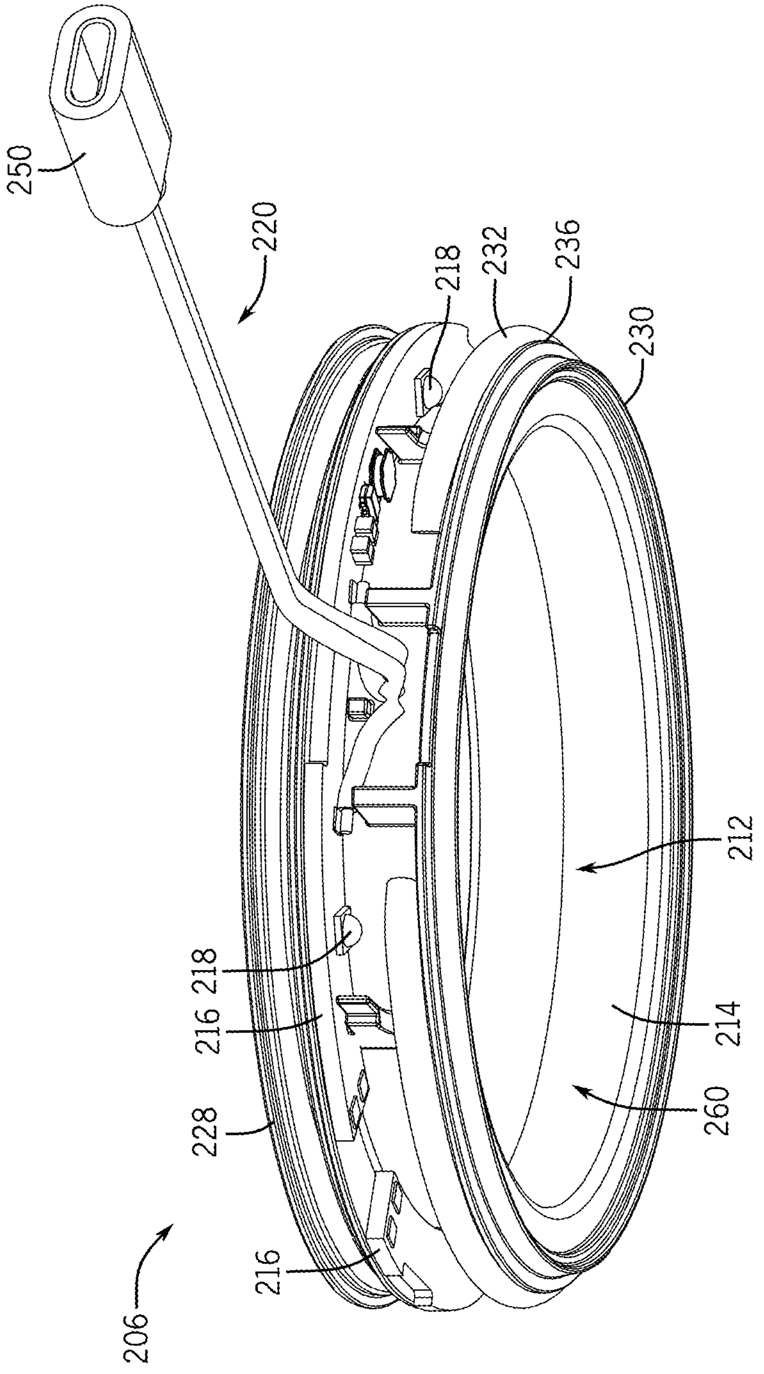
FIG. 6 illustrates a lens assembly of the sink flange of FIGS. 3-5.
Figure 7:
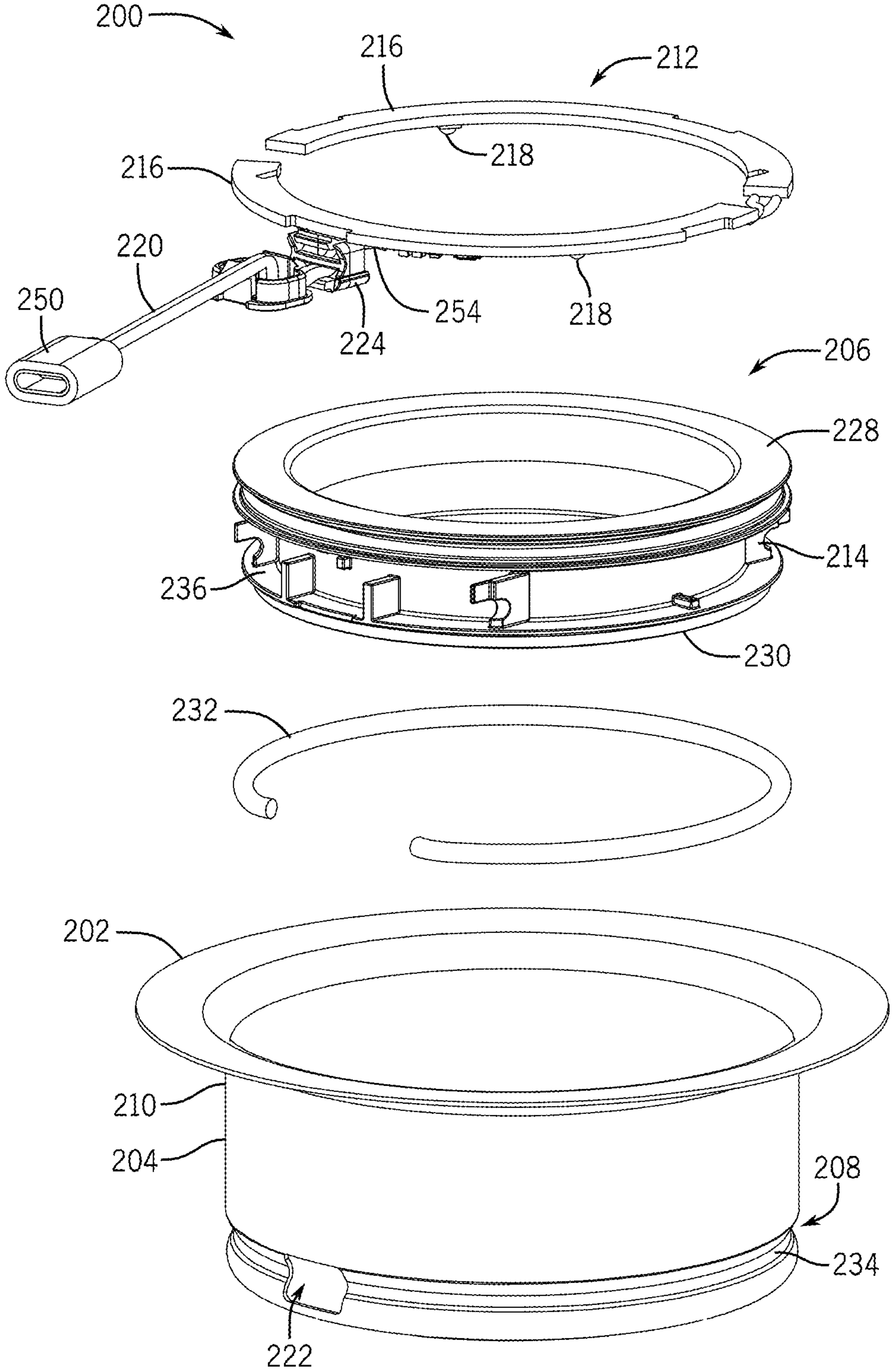
FIG. 7 illustrates an exploded view of the sink flange of FIGS. 3-6.

In the example shown in FIGS. 6 and 7, the lens assembly 206 may also include at least one LED board 216, and as shown includes two curved LED boards 216, each being C-shaped. Each LED board 216 includes a plurality of LEDs 218, and each LED 218 emits violet light. Each LED 218 may be omni-directional, or may be directed to emit violet light over a certain area, such as outwardly from the lens assembly 206 into at least the interior area 212 of the sink flange assembly 200. In some examples, each LED 218 may be configured to emit violet light upwardly and/or downwardly into at least the interior area 212 of the sink flange assembly 200. In some examples the lens 214 may allow for from about 75% to about 100% transmission of the wavelengths of violet light emitted by the LEDs.

The lens assembly 206 may include wire leads 220 connected to the at least one LED board 216, or to each LED board 216, that provide power to each LED 218 when connected to a suitable power supply (not shown), such as a power supply that plugs into a standard wall outlet. In at least some examples, the lens assembly 206 may include a connector 250 attached to the wire leads 220. The connector 250 may be any suitable connector, and may be configured to connect directly to a power supply (not shown), or to a power cable that connects to a power supply. For example, as shown in FIG. 6, the connector 250 is a USB connector, and may be a USB-C connector. In such as example, the power supply may be a 5 volt USB power supply (not shown), and a USB to USB-C power cable (not shown) may be provided to connect the power supply to the connector 250.

In the example illustrated in FIGS. 6 and 7, there are six LEDs 218 in the lens assembly 206. It should be understood, however, that any suitable number of LEDs may be used, such as from one to twelve LEDs, or any other suitable number. The number of LEDs may be constrained based on considerations of providing a sufficient number of LEDs to provide an effective coverage and amount of violet light given factors such as the strength of light being provided and the direction of the light being emitted.

Figure 8:
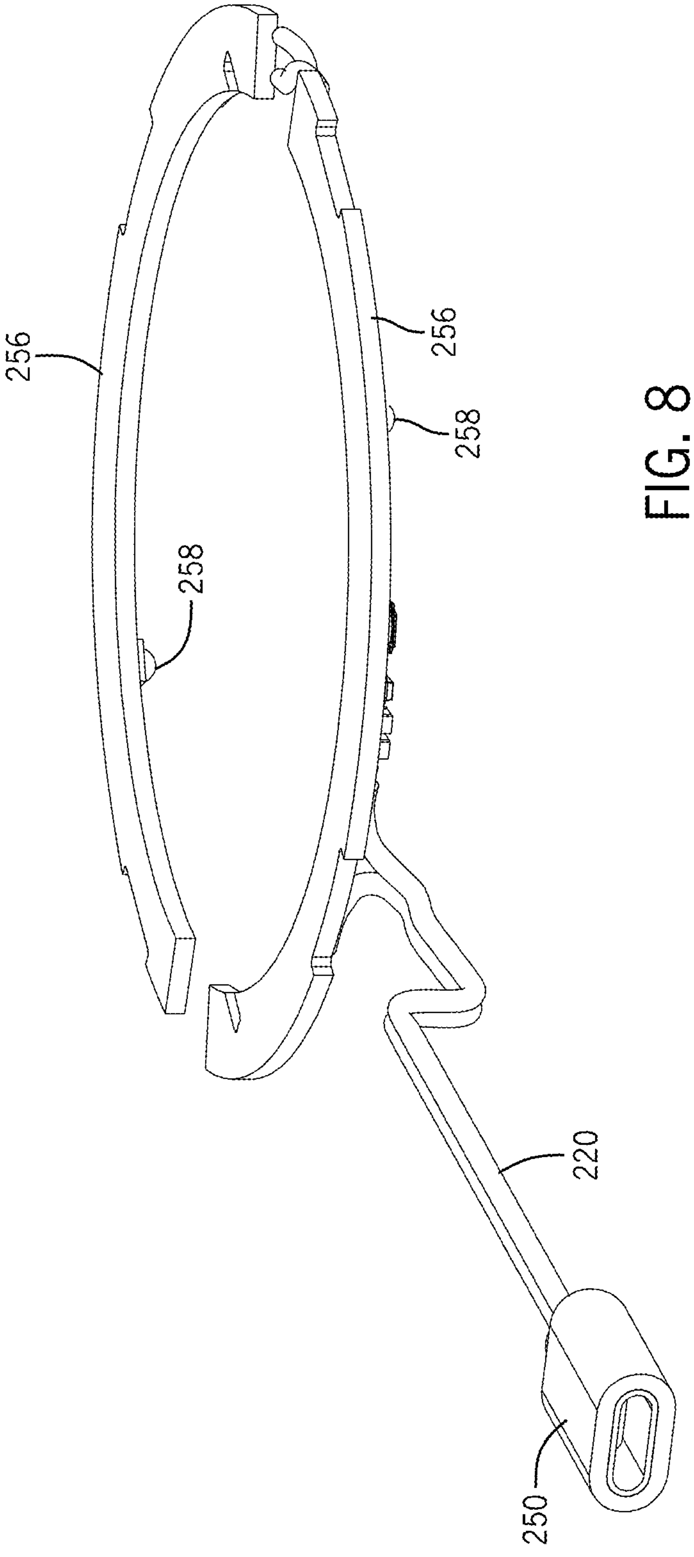
FIG. 8 illustrates an alternative example of a set of LED boards for a lens assembly of the sink flange of FIGS. 3-7.
Figure 9:
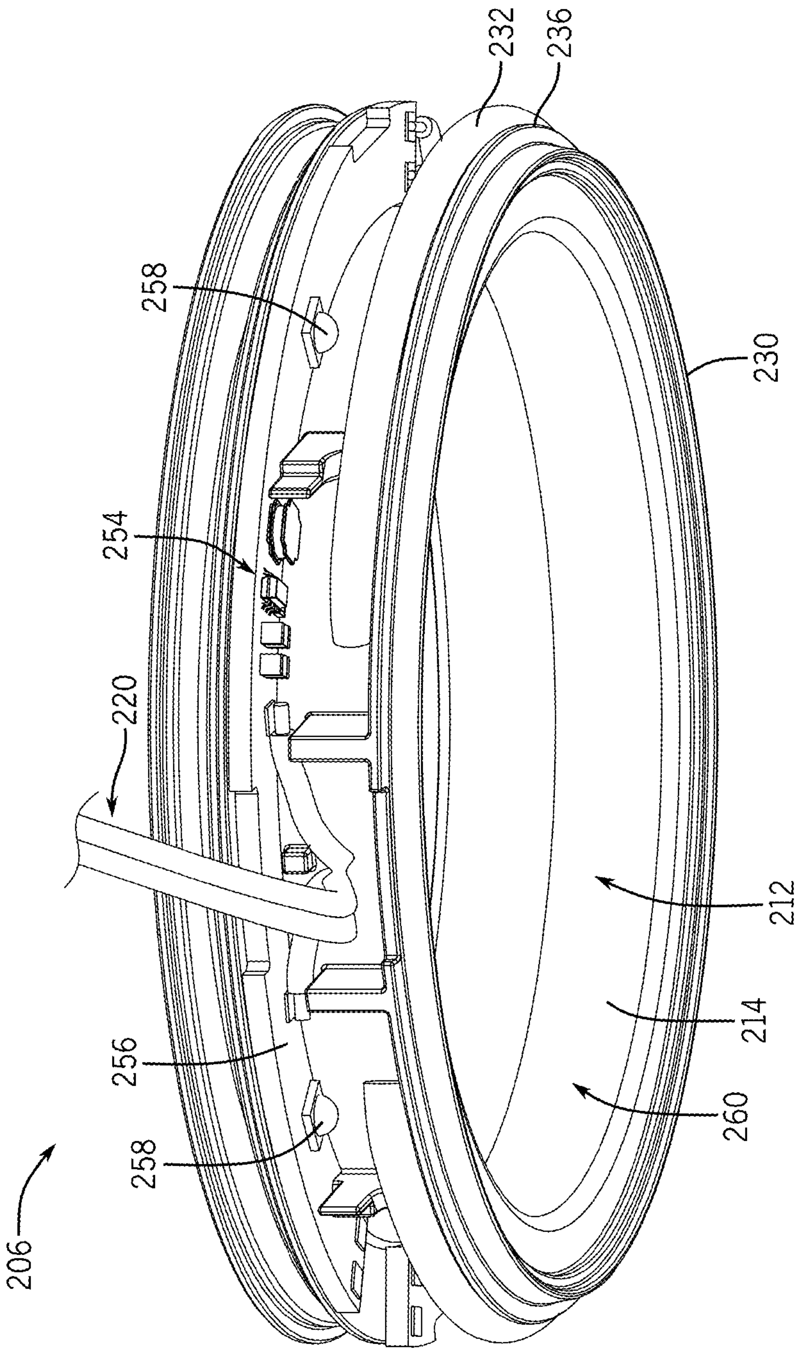
FIG. 9 illustrates a lens assembly of FIG. 6 including the alternative example of a set of LED boards of FIG. 78.

FIGS. 8 and 9 illustrate a lens assembly 206 having an alternative example of a set of LED boards 256, which may be structurally the same as or similar to the LED board 216, except that each LED board 256 only has two LEDs 258, which results in providing a total of four LEDs 258 in the lens assembly 206.

Referring to FIGS. 7 and 9, the lens assembly 206 may include at least one power conversion circuit 254. In some examples, such as the example shown in FIG. 7 having six LEDs 218, a power conversion circuit 254 may be provided on each LED board 216, resulting in the lens assembly including two power conversion circuits 254. In other examples, such as the example shown in FIG. 9 having four LEDs 258, a power conversion circuit 254 may be provided on only one LED board 256, resulting in the lens assembly including only one power conversion circuit 254.

The amount of light output and power usage of lens assemblies of the present technology may be varied. For example, in a constructed prototype of the lens assembly 206 of FIGS. 8 and 89, having four LEDs 258, the total light output in the lens assembly was reduced by 25% as compared to the light output of a constructed prototype of the lens assembly 206 of FIGS. 6 and 7 having six LEDs 218. To achieve the 25% reduction in light output with a 33% less LED count (i.e., four LEDs instead of six), each of the four LEDs 258 actually had a higher light output than each of the sic LEDs 218. The output was adjusted by increasing the current output of the driver circuit 254 on the LED board 256.

In examples where the power supply is a 5 volt power supply, the power conversion circuit 254 may convert the 5 volt input to the voltage needed for the LEDs. In examples having six LEDs 218, as shown in FIGS. 6 and 7, the voltage needed for the LEDs 218 may be in the range of about 9 volts to about 10 volts. Alternatively, in examples having four LEDs as shown in FIGS. 8 and 9, may be about 12.9 volts. The power conversion circuit 254 may adjust the voltage provided to the LEDs 218/268 as needed to maintain a constant current, which may result in maintaining a consistent light intensity.

Referring to FIGS. 6 through 89, in some examples, the LEDs 218/258 may be powered on continuously when the wire leads are connected to a to a suitable power supply (not shown). In other examples, a switch (not shown) may be provided, such that the LEDs 218/258 may be powered on or off by a user.

Figure 4:
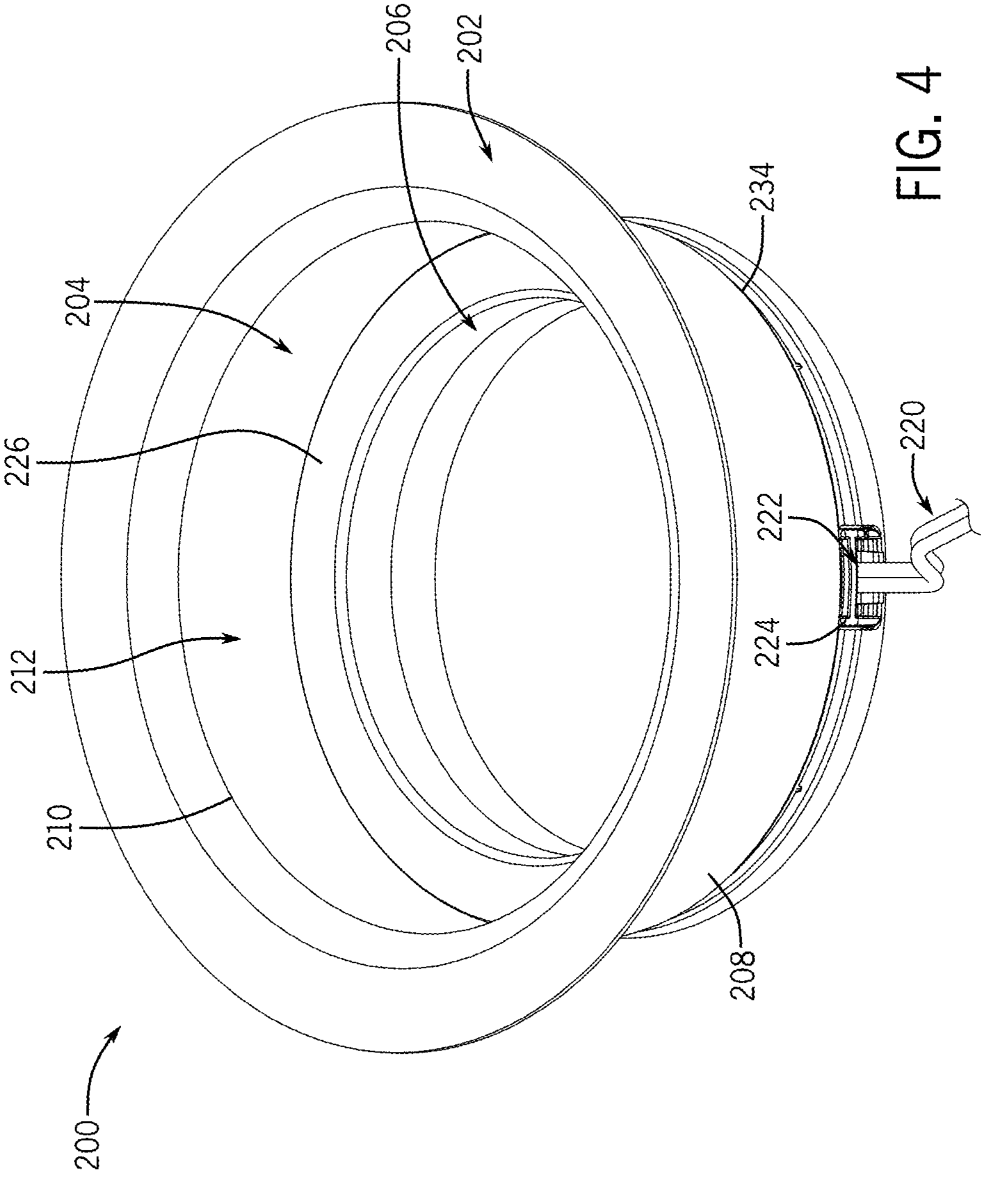
FIG. 4 illustrates a top perspective view of the sink flange of FIG. 3.
Figure 5:
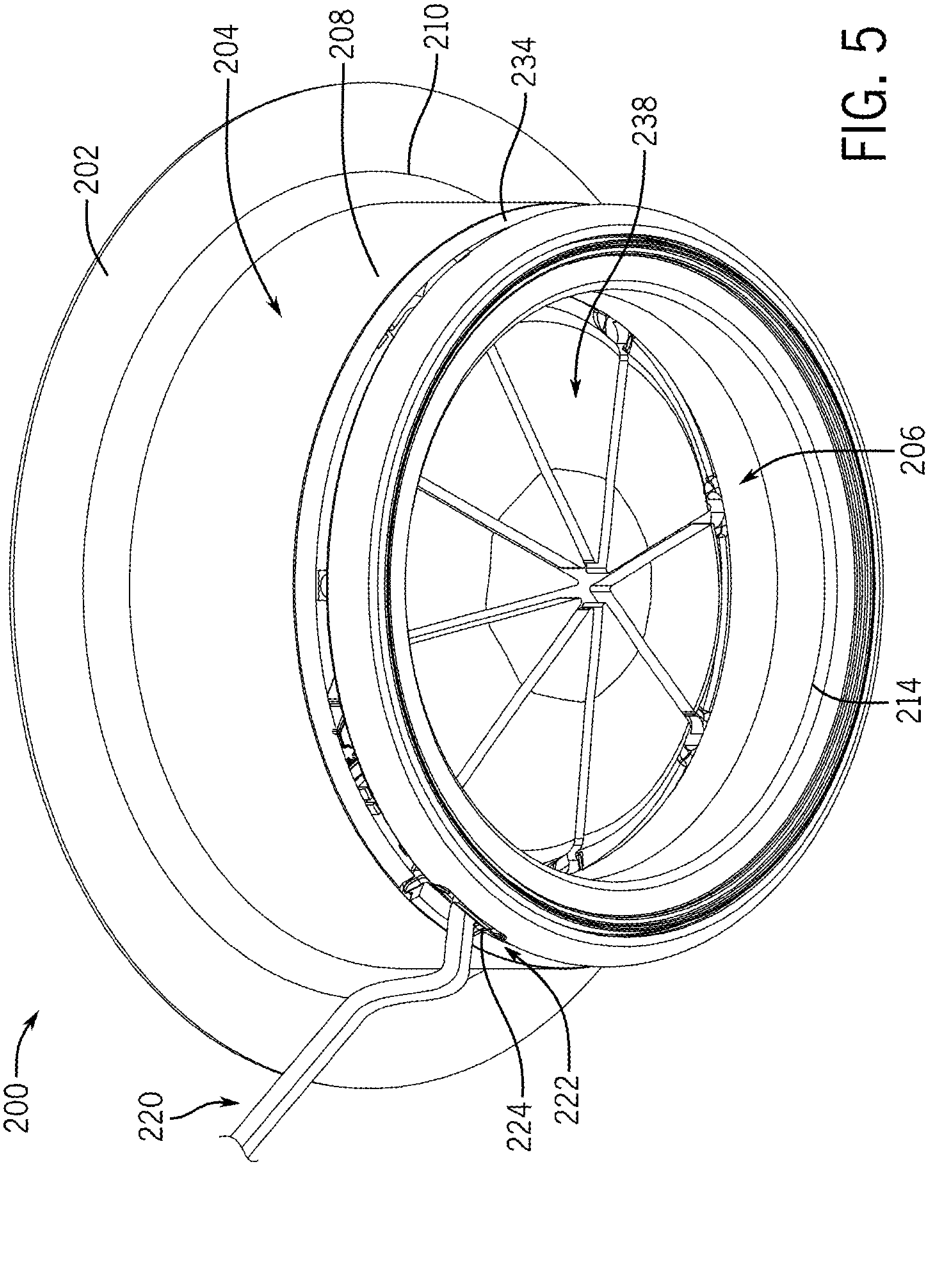
FIG. 5 illustrates a bottom perspective view of the sink flange of FIGS. 3-4, with a baffle included.

As best shown in FIGS. 4, 5 and 7, the sink flange assembly 200 may include a sidewall port 222 in the lower portion 208 of the sidewall 204, and the wire leads 220 may extend through the sidewall port 222 to connect to the power supply (not shown). A seal 224 may be provided in the sidewall port 222, and the wire leads 220 may extend through the seal 224. The seal 224 may be configured to prevent the wire leads 220 from being cut by any sharp edge of the sidewall port 222, and/or to water and food waste from entering the lens assembly 206. The seal 224 may be structured to direct the wire leads 220 under the snap ring 232. The seal 224 may be any suitable seal, such as a rubber grommet, or plastic grommet.

The lens assembly 206 may include one or more seals, which may be rubber seals, and may be separate pieces or overmold seals, for sealing the lens assembly within the sink flange assembly 200. The one or more seals may also assist in preventing water and food waste from entering the lens assembly 206.

As shown in FIG. 4, the sidewall 204 of the sink flange assembly 200 may include an inner ledge 226, which may protrude inwardly into the inner area 212 of the sink flange assembly 200. The lens assembly may be located beneath the inner ledge 226. As shown in FIG. 56, an upper seal 228 may be provided around the top of the lens assembly 206, and may provide a seal between the top of the lens assembly 206 and the inner ledge 226 of the sink flange assembly 200.

As shown in FIGS. 6, 7 and 9, a lower seal 230 may be provided around the bottom of the lens assembly 206. The lower seal 230 may be configured to provide a seal against the rubber disposer mounting gasket when the sink flange assembly 200 is installed as part of a food waste disposer assembly. Alternatively, the bottom of the lens assembly 206 itself may form a seal against the mounting gasket, without the need for a lower seal 230.

Referring to FIGS. 6, 7 and 89, the lens assembly 206 may include a snap ring 232, which may be used to lock the lens assembly 206 in place in the sink flange assembly 200. The lower portion 208 of the sidewall 204 of the sink flange assembly 200 may include a groove 234. The snap ring 230 may fit inside the groove 234. The lens assembly 206 may include a step 236 beneath the snap ring 232, and the step 236 may prevent the snap ring 232 from compressing when an upward force is applied to the lens assembly 206, thereby locking the lens assembly in place.

The sink flange assembly 200 is identical in FIGS. 4 and 5, except that the example in FIG. 5 includes a baffle 238. A baffle within a sink flange assembly 200 may serve one or more purposes. For example, a baffle may reduce noise, and reduce or prevent splash back or particle ejection during disposer operation. Also for example, the baffle may constitute the primary user interface with the disposer, or other plumbing underneath the sink, as food waste must pass through the baffle, usually assisted by the operator, to enter the grind chamber of the disposer. Further for example, the baffle, may prevent foreign objects such as silverware or sponges from entering the disposer or other plumbing underneath the sink.

Referring back to FIG. 3, the sink flange assembly 200 includes an annular ring 202 that is configured to encircle the circular edge of the sink drain when the sink flange assembly 200 is installed in a sink. The sink flange assembly also includes a sidewall 204 that is configured to be inserted and extend through the drain of the sink when the sink flange assembly 200 is installed in a sink. The sidewall 204 is connected to the annular ring 202 at a top edge 210 of the sidewall, which is opposite a lower portion 208 of the sidewall. The sidewall 204 forms an interior area 212, through which water and waste can exit the sink. The sink flange assembly 200 further includes a lens assembly 206, which is attached to, and secured within, the lower portion 208 of the sidewall 204. The sink flange assembly 200 includes a sidewall port 222 in the lower portion 208 of the sidewall 204, and wire leads 220 extend from the lens assembly 206 through the sidewall port 222 to connect to the power supply (not shown). A seal 224 is provided in the sidewall port 222, and the wire leads 220 extend through the seal 224, to prevent water and/or food waste from entering the lens assembly 206. The lower seal 230 of the lens assembly 206 provides a seal against the disposer mounting gasket 306. The lower portion 208 of the sidewall 204 of the sink flange assembly 200 includes a groove 234, and the lens assembly 206 includes a snap ring 232 that fits inside the groove 234, and a step 236 configured to prevent the snap ring 232 from compressing when an upward force is applied to the lens assembly 206.

The baffle 238 is inserted into the sink flange assembly 200, and is located within the sink flange assembly 200 above the lens assembly 206. The circular outer rim 240 of the baffle 238 may be configured to fit within the sidewall 204. In examples where the sidewall 204 of the sink flange assembly 200 includes an inner ledge 226, as shown in FIG. 4, the baffle 238 may rest on top of the inner ledge 226. The baffle 238 may include a circular outer rim 240 and a baffle portion 242 that includes pleats or flaps, such that at least a portion of the baffle portion 242 may drop downwardly when pressure is applied, such as by food waste falling or being pushed through the baffle 238. The baffle portion 242 has an underside 248, which faces downwardly. While any suitable type of baffle may be used, in the illustrated example, the baffle portion 242 includes a plurality of flaps 244, and each flap 244 is connected to the circular outer rim 240 by a hinge 246.

The lens assembly 206 includes LEDs, such as LEDs 218 shown in FIGS. 6 and 67, that emit violet light into the inner area 212 of the sink flange assembly. In this example, each LED 218 is configured to emit violet light upwardly and/or downwardly into at least the interior area 212 of the sink flange assembly 200. The violet light emitted from the lens assembly 206 is directed onto the underside 248 of the baffle portion 242 of the baffle 238. In at least some examples, the violet light emitted from the lens assembly 206 may be directed upwardly by reflecting off of the snap ring 232 and/or other portions of the sink flange assembly 200 and onto the underside 248 of the baffle portion 242 of the baffle 238. The violet light emitted from the lens assembly 206 is also directed downwardly into the disposer 302, and preferably into the grind chamber (not shown) of the disposer 302. In at least some examples, the violet light emitted from the lens assembly 206 is directed at a plurality of angles, such that the violet light covers all areas inside the grind chamber of the disposer.

Figure 10:
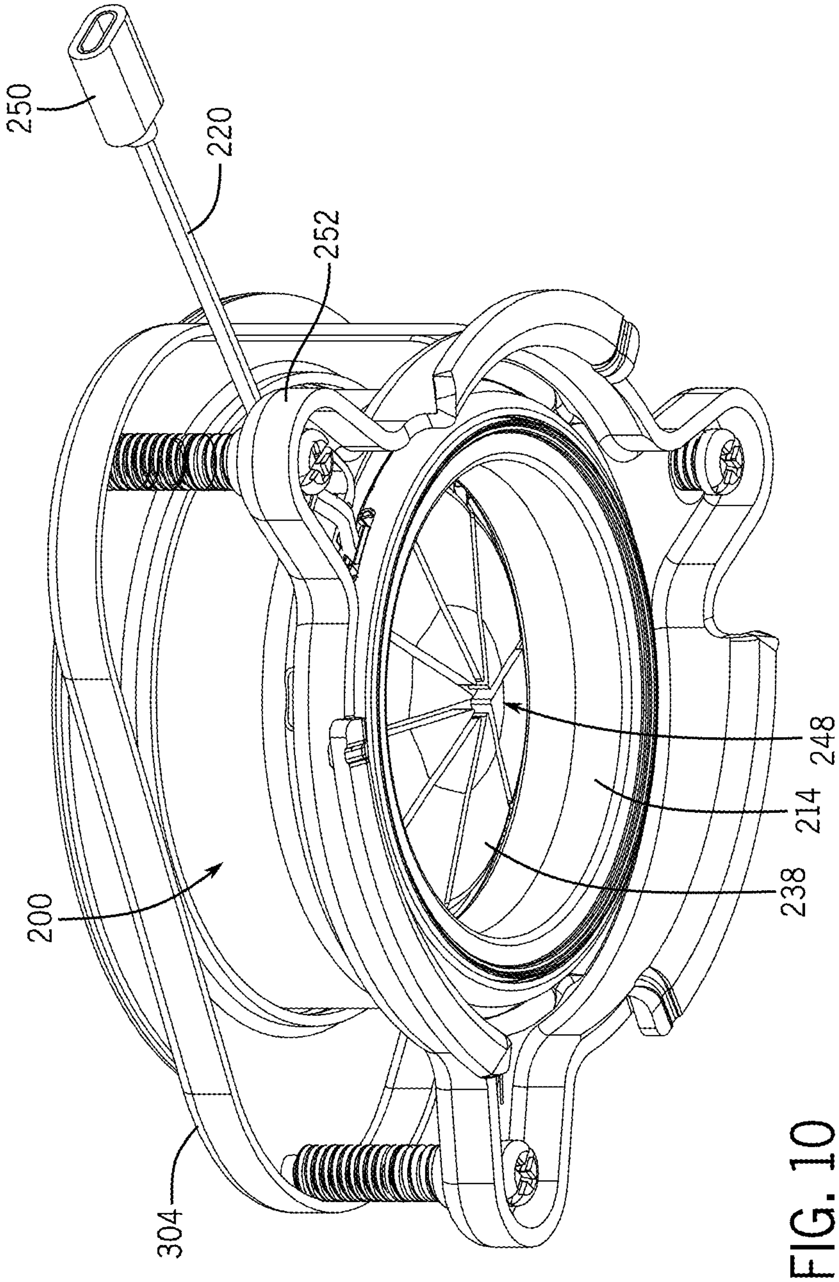
FIG. 10 illustrates a bottom perspective view of one example of the sink flange and disposer mounting assembly of FIG. 3, with a wire clip.

FIG. 10 illustrates one example of the sink flange assembly 200 and disposer mounting assembly 304 of FIG. 3, with a wire clip 252. The primary purpose of the wire clip 252 may be to position the lead wires 220 and hold them outwardly, so that they are clear of the mounting assembly 304 during disposer installation. The wire clip 252 may be mountable to the mounting assembly. The wire clip 252 may be made of any suitable material, including, for example, plastic.

Figure 11:
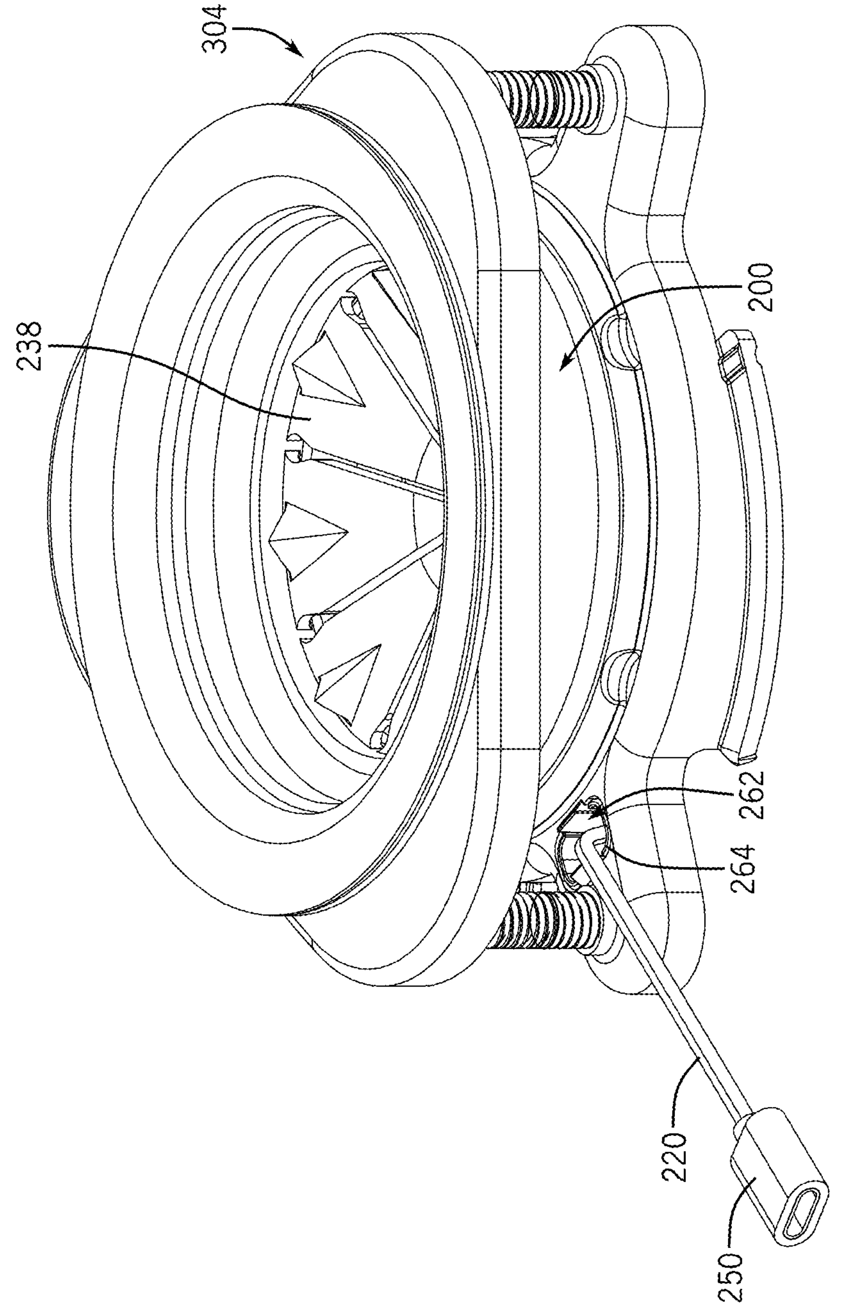
FIG. 11 illustrates a top perspective view of an alternative example of the sink flange and disposer mounting assembly of FIG. 3, with a mounting flange wire port.

FIG. 11 illustrates an alternative example of the sink flange assembly 200 and disposer mounting assembly 304 of FIG. 9, with mounting gasket port 262 instead of a wire clip 252. As with the wire clip 252, the primary purpose of the mounting gasket port 262 may be to position the lead wires 220 and hold them outwardly, so that they are clear of the mounting assembly 304 during disposer installation. The mounting assembly 304 may include a lower mounting flange 306, and the mounting gasket port 262 may be formed in the lower mounting flange 306. For example, the mounting gasket port 262 may be formed by providing a hole in the lower mounting flange 306. Such a hole may be provided in any suitable manner, such as being molded, or by use of a hole punch. As with the sidewall port 22, a seal 264 may be provided in the mounting gasket port 262, and the wire leads 220 may extend through the seal 264. The seal 264 may be configured to prevent the wire leads 220 from being cut by any sharp edge of the mounting gasket port 262. The seal 264 may be any suitable seal, such as a rubber grommet, or plastic grommet.

FIGS. 12 and 13 show another example of a waste disposer system 400 of the present technology that has a lens assembly 402 of the present technology secured to a portion of the waste disposer. As shown, the waste disposer system 400 includes a waste disposer 404, a mounting assembly 406 (FIG. 12) that is configured to mount the waste disposer to a sink, and the lens assembly 402. As shown in FIG. 12, the mounting assembly 406 includes a sink flange assembly 408 and a mounting gasket 410 that connects the sink flange assembly 408 to the waste disposer 404. Referring to FIGS. 12 and 13, the waste disposer includes an upper portion 412 having an outer wall 414 and a first interior area 416 (FIG. 13). As shown in FIG. 13, the outer wall 414 of the upper portion 412 includes at least one window 418, and as shown includes a plurality of windows 418. Referring to FIGS. 12 and 13, the lens assembly 402 includes at least one lens 420, and as shown includes a plurality of interconnected lenses 420. Each lens 420 is secured to a window 418 in the upper portion 412 of the waste disposer 404.

Referring to FIG. 13, each lens 420 has an inner wall 422 that is configured to face into the first interior area 416. Each lens 420 has at least one LED board 424 that includes the at least one LED 426 that emits antimicrobial light, such as violet light. The antimicrobial light may be directed into at least the first interior area 416.

The waste disposer 404 also includes a grinding section 428 below the upper portion 412. The grinding section 428 may have a second interior area 430 that is open to the first interior area 416 of the upper portion 412. In at least some examples, at least one LED 426 of the lens assembly 402 may emit antimicrobial light that is directed into the second interior area.

Referring to FIG. 12, the lens assembly 402 may include wire leads 432 connected to the at least one LED board 424, or to each LED board 424, that provide power to each LED 426 when connected to a suitable power supply (not shown), such as a power supply that plugs into a standard wall outlet. In at least some examples, the lens assembly 402 may include a connector 434 attached to the wire leads 432. The connector 434 may be any suitable connector, and may be configured to connect directly to a power supply (not shown), or to a power cable that connects to a power supply. For example, as shown in FIG. 12, the connector 434 may be a USB connector, such as a USB-C connector. In such an example, the power supply may be a 5 volt USB power supply (not shown), and a USB to USB-C power cable (not shown) may be provided to connect the power supply to the connector 434.

FIG. 14 shows another example of a waste disposer system 500 of the present technology that has a lens assembly 502. As shown, the waste disposer system 500 includes a waste disposer 504, a mounting assembly 506 that is configured to mount the waste disposer to a sink, and the lens assembly 502. The mounting assembly 506 includes a sink flange assembly 508 and a mounting gasket 510 that indirectly connects the sink flange assembly 508 to the waste disposer 504 via the lens assembly 502.

As shown in FIG. 14, the lens assembly 502 is provided in an extension tube 512. The extension tube 512 has first end 514 and a second end 516. When the extension tube 512 is installed, the first end 512 is secured to the mounting gasket and the second end 516 secured to the waste disposer. The lens assembly 502 includes a lens 518 that forms an inner wall 520 of the lens assembly 502 and is configured to face into an interior area of the waste disposer system, specifically at least into an interior area 526 of the extension tube 512 defined by the inner wall 520. The lens assembly 502 includes at least one LED board 522 that includes the at least one LED 524 that emits antimicrobial light, such as violet light. The lens assembly 502 may include wire leads (not shown) and a connector (not shown) in the same manner as discussed above with respect to the other lens assemblies 206 and 402.

Figure 15:
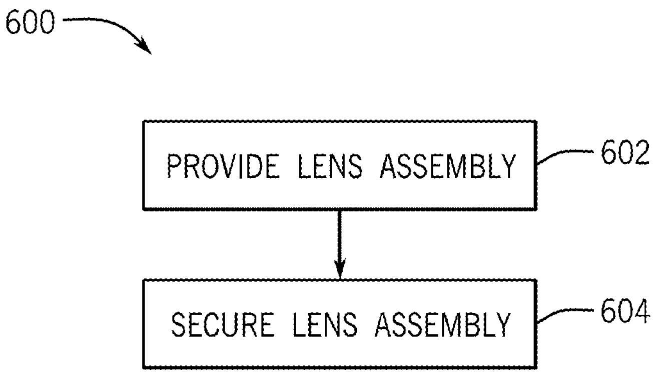
FIG. 15 illustrates a method of installing antimicrobial light into a waste disposer system of the present technology.

FIG. 15 illustrates a method 600 of installing antimicrobial light into a waste disposer system of the present technology. As discussed above, waste disposer systems of the present technology for which this method may be used may include a waste disposer and a mounting assembly configured to mount the waste disposer to a sink, where the mounting assembly includes a sink flange assembly and a mounting gasket that connects the sink flange assembly to the waste disposer. The method 600 may start at step 602, which includes providing a lens assembly. The lens assembly includes a lens that forms an inner wall of the lens assembly and faces into the interior area, and at least one LED board including at least one LED that emit violet light. The method may continue to step 604, which includes securing the lens assembly to at least one of the waste disposer, the sink flange or the mounting gasket.

In at least some examples where the lens assembly is installed in a sink flange assembly, step 602 may include providing a sink flange assembly. The sink flange assembly may be of the type described with respect to FIGS. 3-11. The sink flange assembly may include an annular ring and a sidewall connected to the annular ring at a top edge of the sidewall. The sidewall may extend downwardly from the annular ring, defining an interior area, and including a lower portion opposite the top edge.

Step 602 may also include providing a lens assembly of the type described with respect to FIGS. 3-11. The lens assembly may include a lens that forms an inner wall of the lens assembly and faces into the interior area, at least one LED board including a plurality of LEDs that emit violet light.

Step 604 may include inserting the lens assembly into the sink flange such that the lens assembly is secured within the lower portion of the sink flange. In some examples, where the sink flange assembly is installed with a waste disposer, the method may further include connecting the sink flange assembly to a waste disposer and a mounting gasket.

In at least some examples where the lens assembly is installed on the waste disposer, and the waste disposer includes an upper portion having an outer wall and the interior area, the outer wall of the upper portion including at least one window, step 604 may include securing the lens assembly to the at least one window securing the lens assembly to the at least one window.

In at least some examples where the lens assembly is provided in an extension tube, step 604 may include securing a first end of the extension tube to the mounting gasket, and securing a second end of the extension tube to the waste disposer.

Test

A sink flange assembly 200 was installed as part of a food waste disposer assembly, as shown and described with respect to FIG. 7. The lens assembly was left on for a period of 24 hours, with the violet light being directed onto the underside of the baffle portion of the baffle and into the grind chamber of the disposer. Testing of the amount of odor causing bacteria indicated that from about 97% to about 99% of the odor causing bacteria were killed within the 24-hour testing period.

In view of the foregoing discussion, it should be evident that the present technology includes various examples of waste disposer systems having antimicrobial lighting, lens assemblies that include antimicrobial lighting for use in waste disposers, and methods of installing antimicrobial lighting in waste disposers are provided.

In at least a first embodiment, a waste disposer system having anti-microbial lighting is provided, the waste disposer system comprising: a waste disposer; a mounting assembly configured to mount the waste disposer to a sink, the mounting assembly comprising a sink flange assembly and a mounting gasket that connects the sink flange assembly to the waste disposer; and a lens assembly secured to at least one of the waste disposer, the sink flange or the mounting gasket, the lens assembly including at least one lens that forms an inner wall of the lens assembly and faces into an interior area of the waste disposer system, and at least one LED board including at least one light emitting diode that emits violet light.

In at least a second embodiment, a lens assembly for use in a waste disposer system is provided, the lens assembly comprising: at least one lens that forms an inner wall of the lens assembly and is configured to face into an interior area of the waste disposer system; and at least one LED board including at least one light emitting diode that emits violet light.

The waste disposer system and lens assembly as described with respect to the first and second embodiments discussed above may include other features. For example, the lens may be made of clear plastic. As another example, the at least one LED board may include a plurality of LEDs.

In some examples of the first and second embodiments discussed above, a sink flange may be included that comprises an annular ring and a sidewall connected to the annular ring at a top edge of the sidewall, the sidewall extending downwardly from the annular ring, defining the interior area, and including a lower portion opposite the top edge. In such as example, the lens assembly may be secured within the lower portion of the sidewall. The sink flange may include a baffle having an outer rim and a baffle portion located above the lens assembly in the sink flange assembly, the baffle portion may have an underside and at least a portion of the violet light may be directed onto the underside of the baffle portion. The sidewall of the sink flange assembly may include an inner ledge that protrudes inwardly into the inner area, the lens assembly may be located beneath the inner ledge, and the lens assembly may include an upper seal around the top of the lens assembly that provides a seal between the top of the lens assembly and the inner ledge. The lens assembly may include a lower seal that provides a seal against the mounting gasket.

In some examples of the first and second embodiments discussed above, the waste disposer may include an upper portion having an outer wall and the interior area, where the outer wall of the upper portion includes at least one window, and the lens assembly may be secured to the at least one window.

In some examples of the first and second embodiments discussed above, an extension tube may be included, where the extension tube has a first end secured to the mounting gasket and a second end secured to the waste disposer, and the extension tube includes the lens assembly.

In a third aspect, a method of installing antimicrobial lighting in a waste disposer system that includes a waste disposer and a mounting assembly configured to mount the waste disposer to a sink is provided. The mounting assembly comprises a sink flange assembly and a mounting gasket that connects the sink flange assembly to the waste disposer. The method comprises: providing a lens assembly, wherein the lens assembly includes a lens that forms an inner wall of the lens assembly and faces into the interior area, and at least one LED board including at least one LED that emit violet light; and securing the lens assembly to at least one of the waste disposer, the sink flange or the mounting gasket. In at least one example of the method where the lens assembly is provided in a sink flange assembly, the sink flange assembly may include an annular ring and a sidewall connected to the annular ring at a top edge of the sidewall, the sidewall extending downwardly from the annular ring, defining an interior area, and including a lower portion opposite the top edge. In such an example, securing the lens assembly may include inserting the lens assembly into the sink flange such that the lens assembly is secured within the lower portion of the sink flange. In at least one example of the method where the waste disposer includes an upper portion having an outer wall and the interior area, the outer wall of the upper portion including at least one window, securing the lens assembly may include securing the lens assembly to the at least one window. In at least one example of the method where an extension tube is provided, the extension tube may include the lens assembly, and securing the lens assembly may include securing a first end of the extension tube to the mounting gasket, and securing a second end of the extension tube to the waste disposer.

In some examples where the lens assembly is provided in a sink flange assembly, the waste disposer system may comprise: a waste disposer, a mounting gasket, and a sink flange assembly connected to the waste disposer and the mounting gasket. The sink flange assembly includes an annular ring and a sidewall connected to the annular ring at a top edge of the sidewall, the sidewall extending downwardly from the annular ring, defining an interior area, and including a lower portion opposite the top edge. The sink flange assembly also includes a lens assembly secured within the lower portion of the sidewall, the lens assembly comprising a lens that forms an inner wall of the lens assembly and faces into the interior area, at least one LED board including a plurality of LEDs that emit violet light.

In any of the sink flange assemblies discussed above, the sink flange assembly may include a sidewall port in the lower portion of the sidewall, and wire leads may extend through the hole to connect the lens assembly to a power supply. A seal may be provided in the sidewall port, and the wire leads extend through the seal.

In some examples where the lens assembly is provided in a sink flange assembly, a method of installing antimicrobial lighting in a sink flange may include providing a sink flange assembly, wherein the sink flange assembly includes an annular ring and a sidewall connected to the annular ring at a top edge of the sidewall, the sidewall extending downwardly from the annular ring, defining an interior area, and including a lower portion opposite the top edge. The method may also include providing a lens assembly, wherein the lens assembly includes a lens that forms an inner wall of the lens assembly and faces into the interior area, and at least one LED board including a plurality of LEDs that emit violet light. The method may further include inserting the lens assembly into the sink flange such that the lens assembly is secured within the lower portion of the sink flange.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A sink flange assembly for a waste disposer system, the sink flange assembly comprising:

a sink flange configured to mount to a waste disposer and to a sink;

at least one light emitting diode (LED) configured to emit antimicrobial light, a clear inner wall secured to the sink flange, the clear inner wall configured to direct antimicrobial light from the at least one LED to an interior area of the waste disposer to slow or stop the spread of microorganisms, and a mounting assembly having a mounting gasket that connects the sink flange to the waste disposer, wherein the sink flange includes an annular ring and a sidewall connected to the annular ring at a top edge of the sidewall, the sidewall extending downwardly from the annular ring, defining the interior area, and including a lower portion opposite the top edge; and a lens assembly, including the clear inner wall, secured within the lower portion of the sidewall, and wherein the sink flange includes a baffle having an outer rim and a baffle portion located above the lens assembly in the sink flange assembly, the baffle portion having an underside and at least a portion of the antimicrobial light being directed onto the underside of the baffle portion.

2. The assembly of claim 1, wherein the sidewall of the sink flange assembly includes an inner ledge that protrudes inwardly into the interior area, the lens assembly is located beneath the inner ledge, and the lens assembly includes an upper seal around the top of the lens assembly that provides a seal between the top of the lens assembly and the inner ledge.

3. The assembly of claim 1, wherein the antimicrobial light has a wavelength in the range of 380 nanometers to 750 nanometers.

4. The assembly of claim 1, wherein the antimicrobial light is directed at a plurality of angles to cover the interior area of the disposer.

5. The assembly of claim 1, wherein the clear inner wall is made of clear plastic.

6. The assembly of claim 1, wherein the at least one LED includes a plurality of LEDs.

7. The assembly of claim 1, wherein the waste disposer includes an upper portion having an outer wall and the interior area, the outer wall of the upper portion including at least one window, the lens assembly being secured to the at least one window.

8. A lens assembly for use in a waste disposer system, the lens assembly comprising:

at least one lens that forms an inner wall of the lens assembly and is configured to face into an interior area of the waste disposer system;

at least one LED board including at least one light emitting diode that emits violet light into the waste disposer system to slow or stop the spread of microorganisms; and a sink flange that includes an annular ring and a sidewall connected to the annular ring at a top edge of the sidewall, the sidewall extending downwardly from the annular ring, defining the interior area, and including a lower portion opposite the top edge;

wherein the lens assembly is secured within the lower portion of the sidewall, and wherein the sink flange includes a baffle having an outer rim and a baffle portion located above the lens assembly in the sink flange, the baffle portion having an underside and at least a portion of the violet light being directed onto the underside of the baffle portion.

9. The lens assembly of claim 8, wherein the at least one LED board includes a plurality of LEDs.

10. The lens assembly of claim 9, further comprising a power conversion circuit configured to adjust a voltage based on the power needed for the plurality of LEDs.

11. The lens assembly of claim 10, wherein the power conversion circuit is configured to continuously power the plurality of LEDs.

12. The lens assembly of claim 8, wherein the sidewall of the sink flange includes an inner ledge that protrudes inwardly into the interior area, the lens assembly is located beneath the inner ledge, and the lens assembly includes an upper seal around the top of the lens assembly that provides a seal between the top of the lens assembly and the inner ledge.

13. An assembly for a waste disposer system having anti-microbial lighting, the assembly comprising:

a mounting flange configured to mount a waste disposer to a sink; and a lens assembly secured to the mounting flange and including at least one circuit board including at least one light emitting diode (LED) that emits antimicrobial light into an interior area of the lens assembly to slow or stop the spread of microorganisms, wherein the waste disposer includes an upper portion having an outer wall, the outer wall of the upper portion including at least one window, the lens assembly being secured to the at least one window.

14. The assembly of claim 13, further comprising at least one lens forming a clear inner wall of the lens assembly and configured to face into the interior area of the lens assembly.

15. The assembly of claim 13, wherein the circuit board is at least one LED board including at least one LED.

* * * * *